United States Patent [19]

Niihara et al.

[11] Patent Number: 5,693,671
[45] Date of Patent: Dec. 2, 1997

[54] L-GLUTAMINE THERAPY FOR SICKLE CELL DISEASES AND THALASSEMIA

[75] Inventors: Yukaka Niihara, Rolling Hills Estates; Charles R. Zerez, Culver City; Kouichi R. Tanaka, Rancho Palos Verdes, all of Calif.

[73] Assignee: Harbor-UCLA Research and Education Institute, Torrance, Calif.

[21] Appl. No.: 640,512

[22] Filed: May 1, 1996

[51] Int. Cl.[6] .................................................. A61K 31/195
[52] U.S. Cl. ............................................................ 514/563
[58] Field of Search .............................................. 514/563

[56] References Cited

U.S. PATENT DOCUMENTS

| | | | |
|---|---|---|---|
| 4,261,980 | 4/1981 | Cort | 424/177 |
| 5,108,754 | 4/1992 | Wilburn | 424/422 |
| 5,254,572 | 10/1993 | Serfontein | 514/345 |
| 5,491,150 | 2/1996 | Aoki et al. | 514/310 |

*Primary Examiner*—Raymond Henley, III

[57] ABSTRACT

A method and kit for treating patients suffering from sickle cell disease and thalassemia. The method includes regularly administering a safe and pharmacologically effective amount of L-glutamine based compound to a patient to reduce pain, requirement for pain killers, and increase energy and activity levels.

9 Claims, 7 Drawing Sheets gln = glutamine
glu = glutamate
ppi = pyrophosphate
NA = nicotinic acid
PRPP = Phosphoribosylpyrophosphate NAD metabolism in human erythrocyte Table 1. Glutamine Transport in red blood cells from normal, high reticulocyte and sickle cell anemia individuals.

| Sample Type | Number of Patients | Reticulocyte Count (%) | Hexokinase (μmol/min•10¹⁰ RBC) | Glutamine Transport Rate {Na KRP - choline KRP} (nmol gln/min•ml RBC) |
|---|---|---|---|---|
| NORMAL | | | | |
| Mean ± 1SD | 7 | 1.6 ± 0.3 | 0.29 ± 0.07 | 1.8 ± 0.78 |
| Range | | (1.2 - 2.0) | (0.20 - 0.42) | (1.2 - 3.2) |
| HIGH RETICULOCYTE | | | | |
| Mean ± 1SD | 6 | 9.0 ± 7.8 | 0.82 ± 0.16 | 10.8 ± 9.6 |
| Range | | (4.2 - 24.4) | (0.60 - 1.07) | (3.5 - 29.3) |
| Hb SS | | | | |
| Mean ± 1SD | 11 | 11.4 ± 4.2 | 0.97 ± 0.33 | 31.0 ± 15.3 |
| Range | | (5.7 - 18.6) | (0.51 - 1.76) | (10.1 - 53.6) |

Table 2. Glutamine Transport Km in red blood cells from normal, high reticulocyte and sickle cell anemia individuals.

| Sample Type | Number of Patients | Reticulocyte Count (%) | Hexokinase ($\mu mol/min \cdot 10^{10}$ RBC) | Km ($\mu M$) |
|---|---|---|---|---|
| NORMAL | | | | |
| Mean ± 1SD | 8 | 1.5 ± 0.3 | 0.28 ± 0.06 | 410 ± 165 |
| Range | | (1.2 - 1.9) | (0.24 - 0.40) | (101 - 642) |
| HIGH RETICULOCYTE | | | | |
| Mean ± 1SD | 8 | 5.5 ± 2.4 | 0.65 ± 0.30 | 319 ± 197 |
| Range | | (2.0 - 8.9) | (0.36 - 1.17) | (110 - 635) |
| Hb SS | | | | |
| Mean ± 1SD | 9 | 12.4 ± 4.6 | 1.08 ± 0.16 | 93 ± 59 |
| Range | | (7.7 - 21.7) | (0.84 - 1.38) | (25.1 - 178) |

Table 3. Glutamine and Glutamate levels in red blood cells and plasma from normal, high reticulocyte and sickle cell anemia individuals.

| Sample Type | Number of Patients | Reticulocyte Count (%) | Hexokinase ($\mu$mol/min•$10^{10}$ RBC) |
|---|---|---|---|
| NORMAL | | | |
| Mean ± 1SD | 7 | 1.5 ± 0.3 | 0.27 ± 0.04 |
| Range | | (1.2 - 2.0) | (0.20 - 0.32) |
| HIGH RETICULOCYTE | | | |
| Mean ± 1SD | 5 | 10.9 ± 8.3 | 0.73 ± 0.21 |
| Range | | (4.2 - 24.4) | (0.37 - 0.88) |
| Hb SS | | | |
| Mean ± 1SD | 6 | 8.7 ± 2.4 | 0.85 ± 0.23 |
| Range | | (5.7 - 11.6) | (0.51 - 1.15) |

| Sample Type | Glutamine | | Glutamine | |
|---|---|---|---|---|
| | Plasma ($\mu$M) | RBC ($\mu$M) | Plasma ($\mu$M) | RBC ($\mu$M) |
| NORMAL | | | | |
| Mean ± 1SD | 625 ± 98 | 660 ± 124 | 35 ± 9 | 288 ± 70 |
| Range | (508 - 776) | (556 - 922) | (24 - 50) | (212 - 396) |
| HIGH RETICULOCYTE | | | | |
| Mean ± 1SD | 535 ± 100 | 687 ± 183 | 60 ± 25 | 350 ± 138 |
| Range | (358 - 596) | (496 - 198) | (30 - 92) | (138 - 492) |
| Hb SS | | | | |
| Mean ± 1SD (6) | 697 ± 101 | 867 ± 196 | 50 ± 13 | 549 ± 127 |
| Range | (530 - 796) | (618 - 1090) | (34 - 70) | (434 - 780) |

Table 4. Redox potential and hemoglobin at baseline and after four weeks glutamine administration.

|  | BASELINE (N=5) | WEEK 4 (N=5) | P |
|---|---|---|---|
| Redox Potential (%) | 46.0 ± 2.1 | 67.0 ± 10.6 | <0.005 |
| (Range) | (43.0 - 48.0) | (53.0 - 81.0) | |
| Hemoglobin (gm/dl) | 8.6 ± 1.3 | 8.8 ± 1.4 | n/s |
| (Range) | (7.1 - 10.6) | (7.1 - 10.7) | |

Table 5. Patient M.J. Hemoglobin, hematocrit, RBC count, redox potential.

|  | Hemoglobin (gm/dl) | Hematocrit (%) | RBC ($10^6/\mu l$ blood) | Redox Potential (%) |
|---|---|---|---|---|
| Baseline | 7.1 | 19.5 | 2.34 | 45 |
| Week 4 | 7.1 | 18.5 | 2.30 | 73 |
| Week 8 | 9.1 | 27.0 | 2.91 | 95 |
| Week 12 | 10.4 | 31.0 | 3.42 | 65 |
| Week 24 | 11.3 | 33.5 | 3.59 | 80 |

Table 6. Subjective clinical response in five Hb SS patients after glutamine therapy.

|  | Increased | Decreased | No Change |
|---|---|---|---|
| Energy Level | 5 | 0 | 0 |
| Activity Level | 5 | 0 | 0 |
| Chronic Pain Level | 0 | 5 | 0 |
| Narcotics Dosage | 0 | 4 | 1 |

Adverse reactions: none.

5,693,671

L-GLUTAMINE THERAPY FOR SICKLE CELL DISEASES AND THALASSEMIA

BACKGROUND OF THE INVENTION

1. Field of the Invention

This invention relates to treatments and therapies for anemia conditions and diseases of the blood, and more particular is a therapy for sickle cell diseases and thalassemia by administration of L-glutamine and L-glutamine based compounds.

2. Description of the Prior Art

Sickle cell diseases and thalassemia are some of the most common and devastating hereditary disorders of the blood. Sickle cell disease include diseases which cause sickling of the red blood cells, and includes sickle cell anemia (which results from two hemoglobin S genes), sickle β-thalassemia (one hemoglobin S and one β-thalassemia gene), and hemoglobin SC disease (one hemoglobin S and one hemoglobin C), and the somewhat rare disease hemoglobin C Harlem. Thalassemia includes α-thalassemia and β-thalassemia. These hereditary diseases have significant morbidity and mortality and affect individuals of African American heritage, as well as those of Mediterranean, Middle Eastern, and South East Asian descent. β-thalassemia (also known as Cooley's anemia, erythroblastic anemia, hereditary leptocytosis and Mediterranean disease) in particular affects Eastern descent. These diseases commonly cause severe pain in sufferers in part due to ischemia caused by the damaged red blood cells blocking free flow through the circulatory system.

No safe and effective therapies for these diseases are available. In the past several years, hydroxyurea has been used in an increasing number of sickle cell anemia patients. However, hydroxyurea is a chemotherapeutic agent with myleosuppressive effects and its long term safety is still unknown. An ideal agent would be one that is readily available, affordable, effective and safe even with chronic use.

SUMMARY OF THE INVENTION

The present invention overcomes the above noted deficiencies of the presently available treatments and therapies by providing a novel therapy for sickle cell diseases and thalassemia and other related blood diseases comprising oral administration of a therapeutically effective amount of L-glutamine to patients. The use of the L-isomer is important as the other isomers of glutamine have been known to cause liver damage if taken orally.

The invention further provides a kit for therapy and treatment of sickle cell diseases and thalassemia, and other related blood diseases and conditions.

Figure 1:
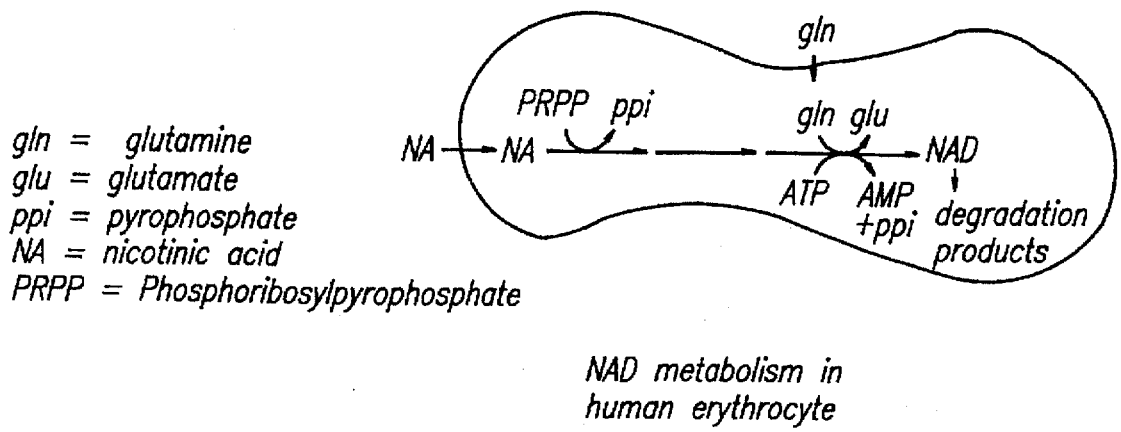
FIG. 1 shows the NAD metabolism in the human erythrocyte.

Table 1 sets forth L-glutamine transport in red blood cells from normal, high reticulocyte and sickle cell anemia individuals.

Table 2 sets forth the L-glutamine transport Michaelis-Menten constant (Km) from normal, high reticulocyte and sickle cell anemia individuals.

Table 3 sets forth glutamine and glutamate levels in RBC and plasma from normal, high reticulocyte and sickle cell anemia individuals.

Table 4 sets forth the redox potential and hemoglobin at baseline and after four weeks of L-glutamine administration.

Table 5 sets forth patient's M. J.'s hemoglobin, hematocrit, RBC count, and redox potential at various weeks.

Table 6 sets forth subjective clinical response in five sickle cell anemia (hemoglobin S) patients after four weeks of L-glutamine administration.

DETAILED DESCRIPTION OF THE INVENTION

Based on previous data from the inventors on sickle red blood cell metabolism, the inventors have conducted a pilot study using L-glutamine as an oral agent. A four week open label study involving five homozygous hemoglobin S (sickle cell anemia) patients showed great promise by demonstrating improvement in redox potential and decrease of chronic pain in all the sickle cell anemia patients. In addition, there were no adverse effects. On the basis of these data, the inventors propose to expand the study of L-glutamine therapy for sickle cell anemia to a double blind study to observe objectively the effect of the amino acid in sickle cell anemia patients in terms of their clinical status and hematological parameters.

The specific aim of these further studies are to determine the effect of oral L-glutamine in treatment of sickle cell anemia in the following areas:

1. Sickle red blood cells at cellular and biochemical level:
   a. Total NAD level and ratio of NADH to total NAD (i.e. NADH+NADH$^+$)
   b. Membrane Iron concentration.
2. Clinical status of the sickle cell anemia patients including the incidence of painful crisis and narcotic requirement for acute or chronic pain.
3. Sickle cell anemia patient's hematological parameters including hemoglobin, hematocrit, reticulocyte count, and hexokinase level.
4. Adverse effects attributable to L-glutamine.

L-glutamine is an amino acid that has been used widely and shown to be safe by others. It is also inexpensive and readily available. The pilot data provides compelling evidence that L-glutamine is useful and safe for the treatment of sickle cell anemia. The inventors believe L-glutamine will also be useful for the other sickle cells diseases and thalassemia as they are believed to result from similar causes, and have a similar metabolic pathway.

a. Background and Significance

Recent studies have shown that oxidative phenomena may play a significant role in the pathophysiology of sickle cell anemia and other related diseases of the blood, such as thalassemia. Several studies have shown that sickle red blood cells (RBC) are more susceptible to oxidant damage than normal RBC.[1–6] This abnormal susceptibility to oxidation by sickle RBC may contribute to the chronic hemolysis[7] and vaso-occlusive events in sickle cell disease.[8]

The pyridine nucleotides, nicotinamide adenine dinucleotide (NAD) and its reduced form NADH play key roles in the regulation and prevention of oxidative damage in RBC. The inventors have found that sickle red cells have a decrease in the NAD/(NADH$^+$+NADH) ratio which they believe may be reflective of increased oxidation in these cells.[9] For example, NADH is required for methemoglobin (met Mb) reduction[10] and also for reduction of oxygen radicals. Furthermore, hemoglobin S has been shown to be more prone to auto-oxidation than hemoglobin A.[11] This adverse effect combined with the susceptibility of sickle RBC to oxidative damage[1-6] places yet further importance on reduction systems in sickle cell disease.

During the past several years, the inventors and others have become increasingly involved in studies of pyridine nucleotide metabolism in sickle RBC. As a result, studies from the laboratory of the inventors and others have shown that the ratio of NAD/(NAD$^+$+NADH) is decreased in sickle RBC.[9] This ratio is an indicator of redox potential and its decrease supports the hypothesis that pyridine nucleotides are involved in the process of oxidant damage in sickle erythrocytes.[9] Another observation from the inventors and others further emphasized the importance of understanding NAD metabolism. It was shown that a decreased NAD/(NAD$^+$+NADH) ratio is one cause of increased 2,3-diphosphoglycerate (2,3-DPG) content in sickle RBC.[12] This, in a way, indirectly related the decreased redox potential to increased sickling in the following manner. With a decrease in redox potential, there is an increase in 2,3-DPG in sickle RBC. With an increase in 2,3-DPG there is an increase in sickling.[12] Therefore, it may be that with a decrease in redox potential, there is an increase in sickling of RBC. These observations prompted the inventors to look at NAD synthesis in sickle RBC hypothesizing that it will be increased. Surprisingly, the results of in vitro studies were unexpected and NAD synthesis was significantly impaired at various steps of synthesis in sickle RBC in vitro, including rate of phosphoribosylpyrophosphate (PRPP) formation and the activity of nicotinic acid phosphoribosyl transferase (NAPRT) which would limit the rate of NAD synthesis in RBC.[13,14]

Nicotinic acid (NA) transport through the RBC membrane, which is the first step in the synthesis of NAD, was also studied by the inventors. There was no significant difference between sickle RBC and control RBC.[15] NAD degradation was also investigated and it appeared to be impaired relative to high reticulocyte control RBC but not enough to explain the degree of change in total NAD content.[14]

Until recently, the only aspect of NAD metabolism which might explain the changes in total NAD content in sickle RBC which had not been examined fully by the inventors or others was glutamine availability. Previously, plasma glutamine levels in sickle cell disease was studied by Enwonwu and colleagues[16], but they did not use high reticulocyte controls which is essential in compensating for the relatively young average cell age of sickle RBC due to the high reticulocyte count. In any case, L-glutamine is required in the last step of NAD synthesis (FIG. 1), and an increase in glutamine availability in vivo could explain the mechanism leading to elevation of total NAD concentration in sickle RBC. The metabolic pathway for sickle cell anemia is believed to be essentially the same or similar to that for the other related sickle cell diseases and for thalassemia, and thus the inventors believe the administration of L-glutamine will be beneficial to sufferers of these diseases.

Recent data from the inventors' laboratory shows that sickle RBC have a several fold increase in the rate of glutamine transport (Table 1) and a significant decrease in the Michaelis-Menten constant (Km) for glutamine transport (Table 2). This is evidence that there is an increased glutamine availability in sickle RBC. In addition, there is a significant increase in RBC content of glutamate, a byproduct of glutamine in NAD synthesis. This is indirect evidence that there is increased utilization of glutamine for NAD synthesis resulting in the elevation of glutamate. These results were consistently observed in the sickle RBC studied with high reticulocyte RBC as controls. Thus, increased glutamine availability in vitro appears to be an important mechanism for the increased total NAD in sickle RBC.

The significance of these data is that glutamine may be used to manipulate the redox status of sickle RBC. Previously, the Michaelis-Menten constant (Km) of glutamine for NAD synthetase[17] has been shown to be significantly higher than the intracellular concentration of glutamine. Therefore, an increase of glutamine concentration in intact sickle RBC is likely to increase the rate of NAD synthetase activity. This will result in an increase of total NAD as well as an increase of NADH. As sickle RBC have been recently shown to have increased transport of glutamine and affinity, additional glutamine in the form of a supplement is likely to increase intracellular availability of glutamine in sickle RBC, and therefore have positive affects.

L-glutamine has been shown to be a safe oral agent by others even at a very high dose.[18,19] It is a tasteless powder that is inexpensive and easy to administer. Based on the current data, the inventors believe the potential clinical effect of this agent by improvement of redox potential may be great. In the recent pilot data as set forth below, the inventors have observed significant improvement in the redox potential as well as subjective positive clinical responses in sickle cell anemia patients.

The inventors have yet to determine the optimal dosage ranges for different patients and different conditions. However, the use of L-glutamine as a treatment for short bowel syndrome, where diarrhea is common (L-glutamine causes some constipation, thus counteracting the diarrhea), dosages of 50 to 60 grams a day have proven safe for long time use. Thus, the inventors believe the use of dosages of L-glutamine at or under 50 to 60 grams a day should be safe. The inventor's have used dosages of 30 grams of L-glutamine a day with good effects, and lower dosages may also be effective. L-glutamine is tasteless, odorless and colorless, and readily dissolves in water, and therefore can be added to water and drank. Also, the inventors believe the L-glutamine can be taken in a capsule form with good results.

Since L-glutamine tends to be relatively unstable when exposed to moisture, the inventors believe the L-glutamine can be conjugated to make it more stable. For example, some forms of N-protected L-glutamine, such as N-acetyl-L-glutamine would be expected to be safe and effective, and have greater stability and shelf-life. Conjugating L-glutamine with another amino acid molecule to form dipeptides, such as Ala-Gln (Alanine-glutamine dipeptide), Gly-Gln L-glycine-glutamine dipeptide) and Gln-Gln (glutamine dipeptide), and others, would be expected to have enhanced stability without loss of efficacy. It is also possible that polypeptides containing glutamine of over two amino acids might also be effective. Hereinafter the term "L-glutamine based compound" shall be meant to encompass L-glutamine and its conjugates.

b. Preliminary Studies

The inventors began studies of glutamine availability in sickle cell anemia by investigating glutamine transport into normal, high reticulocyte (high retic), and sickle RBC. The data showed a several fold increase in RBC active membrane glutamine transport in sickle cell RBC compared to RBC of high reticulocyte controls or normal volunteers.

Figure 2A:
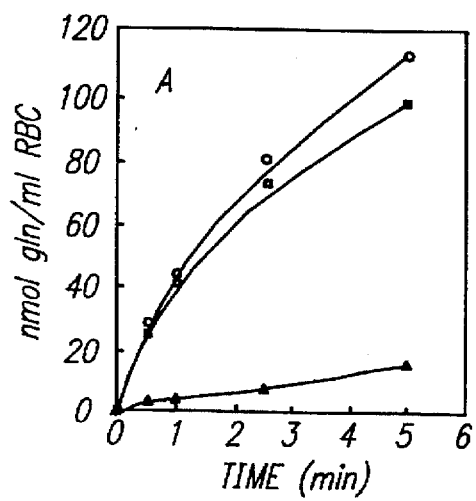
FIGS. 2A and 2B is a comparison of L-glutamine transport assay for typical sickle RBC and high reticulocyte RBC.
Figure 2B:
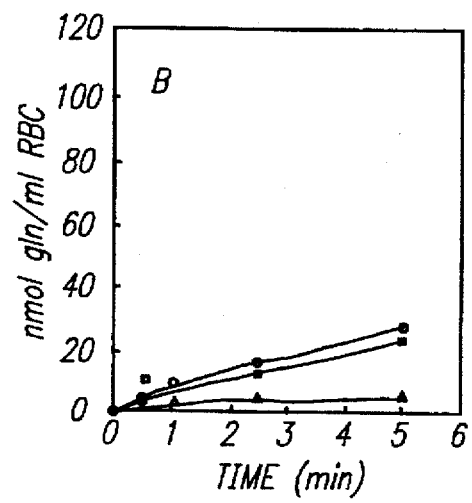
Figure 3:
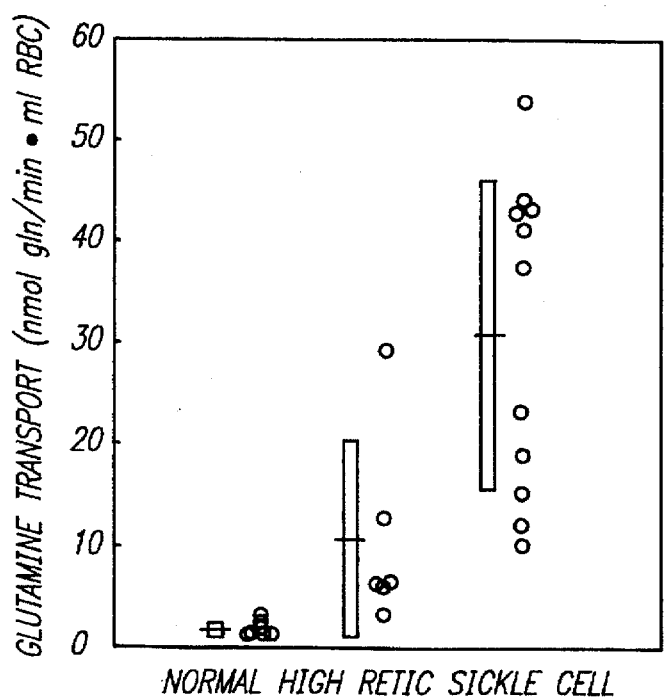
FIG. 3 shows collective data on the rate of L-glutamine transport of normal, high reticulocyte (high retic) and sickle RBC.

Because the active membrane glutamine transport is dependent on Na, the rate of active glutamine transport was determined by subtracting the rate of transport in choline Kreb-Ringer Phosphate (KRP) buffer (representing passive transport) from the rate of transport in Na KRP buffer (representing passive plus active transport). A representative glutamine transport time course in sickle and high reticulocyte RBC of equivalent cell age is shown in FIGS. 2A and 2B. High reticulocyte controls had a significant increase in the rate of active glutamine transport ($P<0.05$), in hexokinase activity ($P<0.00005$) and in reticulocyte counts relative to normal controls which suggest that active glutamine transport is dependent on cell age (Table 1). The rate of active glutamine transport was increased further in sickle RBC compared to high reticulocyte controls ($P<0.02$) whereas reticulocyte counts or hexokinase activity, a good estimate of cell age[21], were not significantly different in these two cohorts ($P>0.2$) (FIG. 3, Table 1). The average rate of glutamine transport is approximately three times higher in sickle cell samples compared to high reticulocyte controls even though the average hexokinase levels and reticulocyte counts are approximately the same. These data suggest that the increase in the rate of glutamine transport in sickle RBC relative to high reticulocyte controls is due to factors other than the RBC's relatively young mean cell age.

Figure 4:
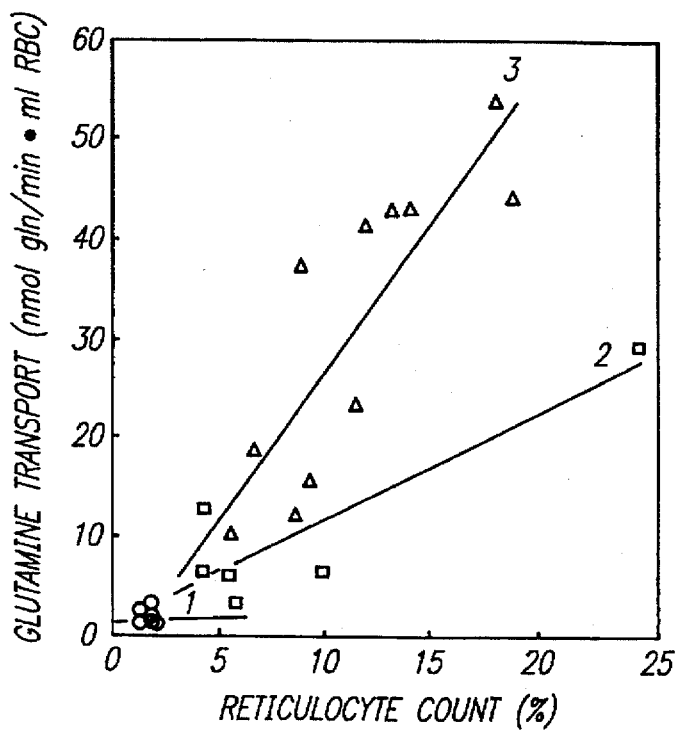
FIG. 4 shows L-glutamine transport vs. reticulocyte count for normal controls, high reticulocyte, and sickle cell patients.
Figure 5:
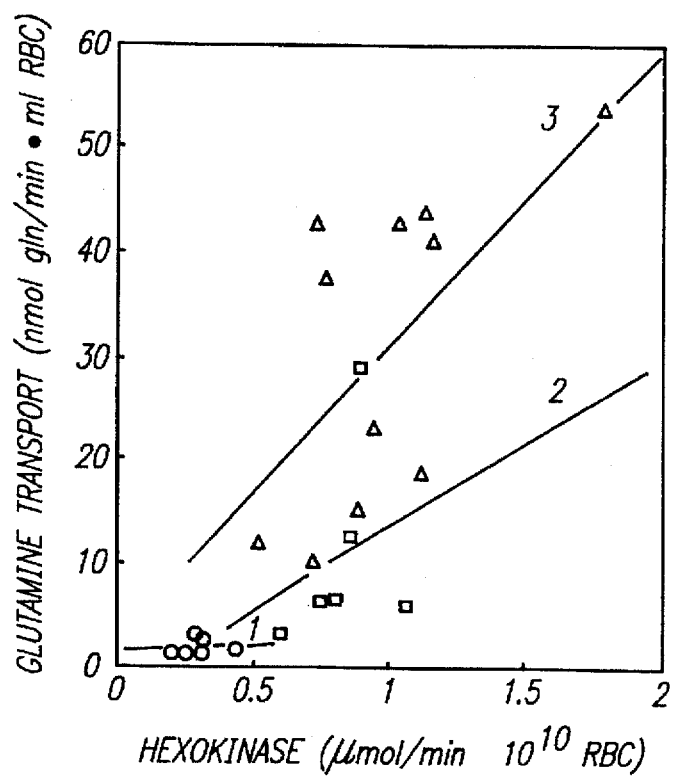
FIG. 5 shows L-glutamine transport vs. hexokinase activity for normal controls, high reticulocyte, and sickle cell patients.

When the rate of glutamine transport is examined as a function of cell age, using either the reticulocyte count (FIG. 4) or the hexokinase activity (FIG. 5), there is a clear linear dependence on cell age. Thus, for any degree of cell age, using either reticulocyte count (FIG. 4) or hexokinase activity (FIG. 5), the glutamine transport rate is higher in sickle cells than in high reticulocyte controls. This is manifested by a higher slope in sickle cells when transport is plotted as a function of cell age (FIGS. 4, 5).

Figure 6:
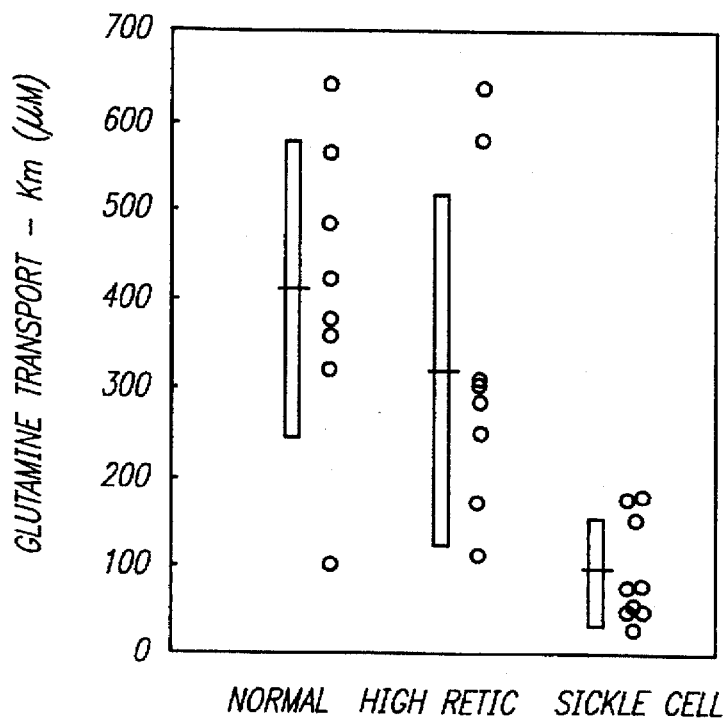
FIG. 6 shows collective data for L-glutamine transport Michaelis-Menten constant (Km) of normal, high reticulocyte and sickle RBC.

To further understand the mechanism of glutamine transport, its Michaelis-Menten constant (Km) was analyzed. The mean for $Km \pm 1$ SD for active glutamine transport in fresh intact red cells was $410 \pm 165$ µM in normal individuals, $319 \pm 197$ µM in high reticulocyte controls and $93 \pm 59$ µM in sickle cell anemia patients (Table 2, FIG. 6). The Km is significantly decreased in the sickle cell group relative to the high reticulocyte group ($P<0.005$) or normal controls ($P<0.0002$).[22] In contrast there is no significant difference between the high reticulocyte group and normal controls ($P>0.2$). Thus, sickle RBC have significantly increased activity for glutamine relative to the other group. Also, these data suggest that young cell age does not appear to play a major role in determining the degree of affinity for glutamine by intact red cells as noted in the similarity of Km between the high reticulocyte group and the normal controls while both their reticulocyte counts and hexokinase levels differed by several fold. It appears from these data that at a given serum glutamine concentration, sickle RBC will have a higher rate of transport compared to the controls.

In an effort to determine whether high in vitro glutamine transport results in significant in vivo glutamine and glutamate changes, the inventors examined glutamine and glutamate levels in freshly obtained blood (Table 3). Red cell glutamate concentrations were $288 \pm 70$, $350 \pm 138$ and $549 \pm 127$ µM in normal individuals, high reticulocyte patients, and sickle cell patients, respectively (Table 3). The data show that there is a significant increase in RBC glutamate ($P<0.02$) in sickle RBC relative to high reticulocyte RBC, while their RBC glutamine levels are similar. Because glutamate is a by-product of glutamine in the synthesis of NAD, this suggests that actively transported glutamine may be readily utilized to form NAD resulting in a significant increase of RBC glutamate level.

In contrast, RBC glutamine levels were $660 \pm 124$, $687 \pm 183$ and $867 \pm 196$ µM in normal individuals, high reticulocyte patients and sickle cell patients, respectively (Table 3). There were no statistically significant differences between the high reticulocyte group and sickle cell group ($P>0.2$). This is also consistent with the inventors' hypothesis that there may be a ready conversion of actively transported glutamine to glutamate in NAD synthesis.

Finally, the plasma glutamine level in sickle patients was significantly elevated relative to the high reticulocyte controls ($P<0.02$).[23] In comparison to normal controls, the sickle cell group showed a trend toward higher plasma glutamine levels. However, the combination of a higher affinity of active red cells glutamine transport system and a higher plasma glutamine concentration relative to the high reticulocyte group is consistent with the hypothesis of increased red cell glutamine availability in sickle cell anemia. Previous data showed that the Km for glutamine in NAD synthesis is significantly higher at $2.17 \pm 0.42$ mmol/L compared to RBC content of glutamine 0.33 nmol/L.[17] Therefore, an increase in RBC content of glutamine is likely to result in further increase of the glutamine utilization for NAD synthesis.

In summary, these data consistently suggest that there is an increased availability and probably utilization of glutamine in sickle RBC in vivo. Since almost all other mechanisms which can lead to increased total NAD were examined and excluded as causes of increased total NAD, glutamine availability is probably the major cause of increased total NAD.

Having answered the above fundamental issues, the inventors have the following two questions. First, with a further increase in availability of glutamine, what will happen to sickle RBC at cellular and biochemical level? Second, how will that affect hematological parameters and clinical status of the sickle cell anemia patients?.

With the data currently in hand, the following hypotheses were drawn:

1. Excess glutamine, a precursor of NAD, will improve the redox potential [i.e. $NADH/(NADH+NAD^+)$].
2. There will be a decrease in membrane iron concentration as a result of the improvement in redox potential.
3. There will be an overall improvement in clinical status of sickle cell anemia patients.

The data from the inventors' pilot study are consistent with the hypothesis. In the pilot trial, five sickle cell anemia (homozygous S) patients who cleared an exclusion criteria participated. The exclusion criteria were: 1) not pregnant, 2) no sickle cell crisis in the previous three weeks, 3) no RBC transfusion in last three months, 4) has not been treated with hydroxyurea within the previous year. Each participant was asked to take 10 grams of L-glutamine three times a day. L-glutamine has been shown to be a safe oral agent at this dose by others.[18,19] After overnight fasting, blood samples were drawn as baseline, and then every week for analysis of redox potential. The summary of the results at the end of four weeks is shown in Table 4.

The inventors have observed a consistent improvement in redox potential to the normal range (50–60%) or above in each patient studied.[24] The mean redox potential after four weeks of administration of L-glutamine was elevated significantly relative to the baseline value. Hemoglobin levels did not change significantly after four weeks of L-glutamine administration. A longer period of observation beyond four weeks may be necessary to determine the effect of L-glutamine on long term RBC survival. One of the patients requested to be on L-glutamine beyond the four week study period. After the approval of the institutional review board, that subject has been continuously taking the L-glutamine beyond the four week period. That patient's baseline hematocrit was 19 percent which had been his usual value for many years according to his clinic records. By the end of the eighth week of L-glutamine administration, the hematocrit had increased to 27 percent. Since then the hematocrit has fluctuated somewhat week to week, but has continued to increase overall. The hematocrit rose to 33.5 percent at week 24. Similar changes were also seen in this patient's hemoglobin level and red blood cell counts (Table 5). Table 5 shows patient M. J.'s Hemoglobin, hematocrit, RBC count, redox potential at various times.

Currently at six months of L-glutamine administration, the patient reports no adverse effects. Instead, the patient claims to have much less chronic pain and decrease in use of pain controlling narcotics. During this period, the patient has not been hospitalized at all which is a notable improvement for this patient. He had been hospitalized five times in the previous six months prior to L-glutamine administration for sickle cell crises. Clinically, within four weeks, all of the participants reported an improvement of overall energy level, accompanied by increased activity level. Although the inventors cannot yet absolutely attribute the above clinical changes to the effect of glutamine upon RBC, nonetheless the clinical effect was significant and positive. In addition, each patient also noted various degrees of decrease in chronic pain. Four of the five patients decreased usage of pain controlling narcotics. The one patient who did not suffered from other chronic pain. No adverse effects of L-glutamine were reported by any of the patients (Table 6).

C. Prophetic Studies

Based upon these data from the pilot trial the studies will be expanded to 1) confirm the results of the clinical response observed in the pilot study by conducting a double blinded study, 2) further examine the mechanism that induces elevation of redox potential in sickle RBC, 3) observe the clinical effect of longer duration of L-glutamine administration with emphasis on frequency of crises, major sickle cell complications such as stroke, and narcotic requirements, 4) observe for possible adverse effects of L-glutamine over long period of time, and 5) examine the clinical effects in other groups of patients such as hemoglobin SC and sickle-β thalassemia.

In the present application, the inventors propose to further investigate in vivo efficacy of orally administered glutamine for therapy of sickle cell anemia and other sickle cell diseases and thalassemia. The following steps will be taken in this study to achieve the specific aims.

1. Administration of Glutamine Supplement

Thirty grams of pure L-glutamine or placebo (corn starch) will be administered orally to each participant daily for 24 weeks. This amino acid at the dose indicated has been shown to be safe for oral administration with essentially no adverse effect.[18, 19] Both L-glutamine and corn starch are white powders with an identical appearance. They are also essentially tasteless. The powders will be packed in clear size 0 gelatin capsules to conceal the texture and any subtle difference in taste of the powders. The Research Pharmacy of Harbor-UCLA Medical Center will prepare and keep the log of the study medication and placebo. Whole blood samples will be drawn for studies of glutamine, glutamate, pyridine nucleotide measurements, incubated Heinz bodies and CBC on days #0, #7, #14, and #28, then weeks #6, #8, #12, #16, #20, and #24. Heinz bodies are granules in red blood cells resulting from damage of the hemoglobin and are an indirect measure of the damage to the blood due to sickle cell disease and thalassemia.

The effect of L-glutamine on hematological parameters and clinical status is likely to be manifested during the study period. Each sample will be drawn after overnight fasting.

2. Plasma and RBC Levels of Glutamine in Sickle Cell

With oral supplementation of L-glutamine, the inventors expect to achieve an increase in intracellular content of RBC glutamine available for NAD synthesis. The measurement of plasma and RBC glutamine levels will provide the inventors with the following information.

i) Patient compliance ii) Effect of oral glutamine on intracellular availability of the amino acid.

With proper administration of the current dose of L-glutamine, the plasma level of the amino acid should increase. With an increase in plasma level of oral L-glutamine, an increase in intracellular availability of L-glutamine for NAD synthesis is expected.

This assay will be conducted by the NIH funded Clinical Research Center of Harbor-UCLA Medical Center without provision of the data to the principal investigator until the end of the study to ensure the double blinded nature of the study.

3. NAD and NADH Measurements

With an increase in the availability of glutamine, NAD synthesis is expected to increase. The investigators will determine whether this will lead to an increase in content of NADH. In this part of the experiment, the investigators will measure intracellular levels of total NAD and NADH. Following these determinations, the ratio of NADH to total NAD will be calculated to measure the effect of glutamine on RBC redox potential. Studies to date have shown that the glutamine supplement increases the redox potential leading to decreased RBC oxidant susceptibility. However, further studies may show that the redox potential may not change significantly and that anti-oxidant effects may be due to the absolute increase in NADH content.

4. Observation of Heinz Bodies

The amount of incubated Heinz bodies observed will serve as an indicator of oxidant damage to RBC. With improvement in redox potential or an increase in NADH content, the number of Heinz bodies is expected to decrease.

5. RBC Membrane Iron

The survival of RBC may not necessarily increase with L-glutamine administration. It is possible that the patient's overall clinical status may improve, because of changes other than the improvement in hemoglobin or hematocrit levels. Some of the changes may be an improvement in the red cell structure but without improvement in RBC survival. Recent literature links deposition of iron on the cytoplasmic surface of the membrane as a result of oxidative insult in sickle RBC.[25,26] Significant changes can occur in membrane content of oxidized iron as a result of the oxidative process. This iron accumulation can change the rigidity of the cell membrane which is thought to play a major role in clinical events by compromising blood flow in the microvasculature. In addition to evaluation of redox potential, analysis of possible changes in membrane iron content with L-glutamine administration will be performed. These data may support the clinical benefit of L-glutamine by showing a decrease in membrane iron with improvement of redox potential.

6. RBC Count, Hematocrit, Reticulocyte Count and Hexokinase Level

These measurements will be used as an indirect measurement of RBC survival. With improvement of RBC survival, RBC count and hematocrit should increase, whereas reticulocyte count and hexokinase level should decrease.

7. Clinical Evaluation of Patients

During each visit on days #0, #7, #14, and #28, then weeks #6, #8, #10, #12, #16, #20, and #24 a careful interview will be conducted to assess any change in each patient's clinical condition. The investigators will note any changes in severity and frequency of chronic or acute pain; the type and amount of daily pain medication requirement, exercise tolerance in terms of distance that they can walk or run without rest, and any other clinical aspects or events that occurred in each patient during the study including hospitalization or visits to emergency rooms.

Blood specimen will be drawn after overnight fasting. Once the specimen is drawn it will be processed immediately for various assays including glutamine levels using the Beckman 6200 amino acid analyzer.

8. Statistical Analysis

Student T test will be utilized for the analysis of data.

9. Potential Difficulties and Limitations, and Alternative Approaches

A. Placebo

Because the dose of the placebo is high to match the study drug, the investigators may have difficulties with the placebo group as they are expected to experience no beneficial effects.

B. Alternative Approach

If compliance becomes a problem to continue the double-blinded study, the following are considered:

a. Gather and synthesize the data up to the point where compliance becomes problematic.
b. Start short-term (4-5 weeks) open label study using a lesser dose of L-glutamine to determine if it can achieve similar changes observed with high dose L-glutamine administration of 30 grams a day.
c. Restart double-blinded study using lower dosage of study medication and placebo according to the result of the open label study.

C. Evaluation of Clinical Response

The evaluation will be mainly based on interviews with the patient upon each visit. The primary care of the participants will continue to be provided by the primary physicians of the patients throughout the study. The data on clinical status will be mainly based on subjective reply of patients. This may result in discrepancy between the data obtained by the investigators and what is noted in the record of the primary physician.

D. Alternative Approach

In the event that such discrepancy becomes apparent and frequent when the data are compared to that of the primary physicians the following measure is planned. The investigators and their consultant, after discussion with the primary physicians of the patients, will assume primary care of the participants for the duration of the study in order to keep better records of the patients' clinical status, prescribed amounts of pain medications, number of crises, hospitalization and other changes.

10. Time Table

During the first year, the investigators will randomize 25 patients. For each patient, complete history including use questionnaires and physical examination are performed on initial visit. This will take approximately two hours. Fasting blood will be drawn for the baseline value at that time. For each subsequent visit, ½ hour will be set aside for questions, limited physical examination including heart, lungs, and the areas of acute or chronic problem(s). Fasting blood samples will be taken upon each visit. With all the assays outlined in this proposal, an estimated two working days will be required for a research associate or an investigator to perform all of them for each blood sample. The investigators plan on enrolling one new patient every two weeks so that there will be about six to seven patients to study per week when 25 patients are enrolled.

The recruitment of patients will continue through the beginning of the third year in order to randomize an additional 35 patients. The researchers' goal is to randomize a total of 55–60 patients. The protocol on the last patient is expected to be completed during the second half of the third year. The last three months will be devoted to summary and interpretation of the collected data by carefully reviewing the record of each participating patient.

11. Study Population:

The participants will be patients with sickle cell anemia (homozygous S). The Hematology Clinic of Harbor-UCLA Medical Center will serve as the major source of individuals with sickle cell anemia. Approximately 30–40 adults (>18 years of age) with sickle cell anemia are followed by the service. Aside from this, the researchers will advertise the project in the community to recruit more patients. According to the registry of the local Sickle Cell Disease Research Foundation, there are more than 200 sickle cell anemia patients who are currently registered in the greater Los Angeles area. The investigators exclusion criteria include, 1) no blood transfusion within three months of the initiation of the study, 2) no crisis within three weeks of the initiation of the study, 3) no hospitalization within a month, 4) not pregnant, and 4) has not been on hydroxyurea for at least one year. Males and females are approximately equally represented. All persons with sickle cell anemia will have the presence of homozygous hemoglobin S documented by hemoglobin electrophoresis.

12. Methods:

A. Administration of L-glutamine and Placebo

After obtaining consent, patients will be given instructions for self administration of pure L-glutamine or placebo 30 grams to be taken orally daily in three divided doses of 10 grams. The Research Pharmacy of Harbor-UCLA Medical Center will randomize the patients and keep the record of study medication. The randomization information will be concealed to the investigators and the patients until the end of the study with exception in the event of emergency in study patient that will require unblinding of the study medications.

B. Blood Samples

Approximately 10 ml of blood will be obtained by routine venipuncture for subsequent processing for metabolic studies on days #0, #7, #14 and #28, then week #6, #8, #12, #16, #20 and #24.

C. Hexokinase Activity

A red cell enriched fraction will be obtained by passing whole blood through a column of α-cellulose and microcrystalline cellulose to deplete white cells and platelets.[27] Erythrocytes will then be washed three times with 0.15M NaCl. Hemolysates will be prepared by the freeze-thaw method and hexokinase activity will be determined spectrophotometrically as described by Beutler.[27]

D. Plasma and RBC Levels or Glutamine

The blood simple will be evenly divided for measuring plasma and whole blood levels of glutamine. Both samples will be promptly processed for determination of glutamine levels using the Beckman 6200 amino acid analyzer. Then, the data obtained will be applied to the following formula to calculate the intraerythrocytic level of glutamine.

Cbc={Cwb−Cp(1−Hct)}+Hct wherein

Cbc=intracellular concentration
Cwb=whole blood concentration
Cp=plasma concentration
Hct=hematocrit

E. NAD and NADH Measurements

The method based on single extraction procedure with spectrophotometric determination described by Zerez et al. will be utilized.[28] In this method, extracts of oxidized and reduced pyridine nucleotides are prepared from whole blood immediately after phlebotomy. To make the extract, whole blood is mixed with a solution containing nicotinamide, $NAHCO_3$, and $Na_2CO_3$. Then, for NADH determination, heat incubation is used to destroy oxidized NAD. For both NAD and NADH extracts, spectrophotometric enzymatic cycling assays are used to determine the levels in respective extracts.

F. RBC Count, Hematocrit

These measurements will be obtained by Coulter counter and microhematocrit centrifuge.

G. Reticulocyte Count

The method using methylene blue will be utilized.[29]

H. Measurement of Membrane Iron

The method described by Repka and colleagues will be used for this assay.[25,30] In this assay, free iron on ghost membrane and inside-out membrane will be determined by its activity with ferrozime (which does not detect heme iron) in the presence of the denaturant sodium dodecyl sulfate (SDS) and the reducing agents ascorbate and sodium metabisulfite. "Free iron" refers to nonheme nonferritin iron that reacts within 2 minutes in the ferrozime assay. The amounts of iron will be expressed in nanomoles of iron per milligram of membrane protein. The membrane protein will be determined by BioRad (Richmond, Calif.) microprotein assay. Reagents used for the measurement of membrane iron will be rendered iron free by treatment with chelating resin (Sigma).

13. Human Subjects

The subject population will consist of individuals with sickle cell anemia (homozygous S). The inventors expect to randomize 60 patients for this project during the proposed period of three years. About equal numbers of male and female individuals will be enrolled in these studies. The age range includes individuals who are 18 years or older. Younger patients, particularly children, are excluded from this project because there is not sufficient information for the dose of the medication for this population. Pregnant patients are also excluded in this study. Although no harm is anticipated to the mothers or fetus using L-glutamine, the inventors plan to gather more information on non-pregnant patients in regard to potential efficacy or adverse effects before studying pregnant patients. Patients who have been transfused within three months, had sickle cell pain crisis within three weeks or had been hospitalized within a month will be excluded from entering the study to minimize the bias on the baseline clinical status and the blood laboratory values. Those who have been on hydroxyurea within the last year will also be excluded.

Each participant will be randomized into L-glutamine or placebo group. Then the participant will be asked to take capsules containing 10 grams of either L-glutamine or placebo three times a day. The blood specimens will be obtained after overnight fasting by routine venipuncture for baseline and then on days #7, #14 and #28, then weeks #4, #6, #8, #12, #16, #20 and #24. At the initial screening visit, the patient will have a complete history and physical examination by the P. I. or co-investigator. Then, on subsequent visits the participant will have focused history and physical examination including interview on their clinical status and possible adverse reactions.

Human peripheral blood will be the only material used in these studies. To minimize the number of venipunctures, blood specimens for research will be obtained at the time for phlebotomy for routine blood studies indicated for patient care if possible. The blood specimens which we use will be purely for research purposes.

Volunteers will be recruited from various sources including the outpatient services of the Department of Medicine of the Harbor-UCLA Medical Center. Also, an announcement will be made locally to attract patients who live within or near the greater Los Angeles area. After screening for inclusion and exclusion criteria, informed consent will be obtained by the P. I. or a designee after the purpose of the research has been explained to the participating individuals in lay language. Consent will be obtained from the participating individuals. An appropriate consent document approved by the Human Subjects Committee of the Harbor-UCLA Medical Center will be signed by each participant prior to phlebotomy.

There are few potential risks to participating in this study. Oral administration of L-glutamine has been used widely and has been shown to be safe by others. The amino acid may cause constipation, otherwise no other known significant adverse reactions are expected. The placebo used in this study, corn starch, also has been used widely and shown to be safe without significant side effects. The risks of venipuncture include infection and bleeding. These risks are considered exceedingly low.

The P. I. or co-investigator is available at all times to the participants. In the event of any significant adverse event, whether it is related to the study or not, the P. I. and the primary physician of the patient will work together to provide the best possible care to the patients. Also, at that time the study medication will be held until it is clear that the study medication is not the cause of the patient's adverse event. If the patient complains of constipation, as the side effect of L-glutamine, the patient will be evaluated and receive appropriate treatment or prescription by the P. I. or his designee, to relieve the constipation. The risks and discomforts of phlebotomy will be minimized by the use of experienced phlebotomists. When possible, blood taken for experimental purposes will be obtained at the same time blood is being withdrawn for routine patient care. Data will be kept confidential and, if published in a scientific journal, will be done without identification of the individual participants.

The risks of significant, adverse reactions with L-glutamine or the placebo, corn starch are essentially none. These are basically nutritional supplements which have been used widely and shown to be extremely safe by others. Also, the risks of venipuncture by an experienced phlebotomist are exceedingly low. Thus, the risk to a participating individual is exceedingly low given the potential clinical benefit and valuable information learned in management of sickle cell anemia. The project will result in new insights toward the management of sickle cell anemia using this extremely safe agent L-glutamine.

These and further studies by the inventors will optimize the dosage requirements and further prove mechanism by which L-glutamine is effective as a therapy for sickle cell anemia and other sickle cell diseases and thalassemia.

The drawings, tables and the foregoing description are not intended to represent the only form of the invention in regard to the details of its manner of operation. In fact, it will be evident to one skilled in the art that modifications and variations may be made without departing from the spirit and scope of the invention. Although specific terms have been employed, they are intended in a generic and descriptive sense only and not for the purpose of limitation, the scope of the invention being delineated in the following the claims which follow.

LITERATURE CITED

1. Asakura T, Minakata D, Adachi K, Russel M O, and Schwartz E: Denatured hemoglobin in sickle erythrocytes. J. Clin Invest 59: 633, 1977.

2. Chiu D, Lubin B, and Shohet S B: Erythrocyte membrane lipid reorganization during the sickling process. Br J Haematol 41: 223, 1979.

3. Das S K and Nair R C: Superoxide dismutase, glutathione peroxidase, catalase and lipid peroxidation of normal and sickled erythrocytes. Br J Haematol 44: 87, 1990.

4. Campwala H Q and Desforges J F: Membrane bound hemochrome in density-separated cohorts of normal (AA)O and sickled (SS) cells. J Lab Clin Med 99: 25, 1982.

5. Hebbel R P, Eaton J W, Balasingam K, and Steinberg M H: Spontaneous oxygen radical generation by sickle erythrocytes. J Clin Invest 70: 1253, 1982.

6. Jain S K and Shohet S B: A novel phospholipid in irreversible sickled cells: Evidence for in vivo peroxidative membrane damage in sickle cell disease. Blood 63: 362, 1994.

7. Bensinger T A and Gillete P N: Hemolysis in sickle cell disease. Arch Int Med 133: 624, 1974.

8. Hebbel R P, Boogaerts M A B, Eaton Y W, and Steinberg M H: Erythrocyte in sickle cell anemia. N Engl J Med 302: 992, 1980.

9. Zerez C R, Lachant N A, Lee S J, and Tanaka K R. Deceased Erythrocyte nicotinamide adenine dinucleotide redox potential and abnormal pyridine nucleotide content in sickle cell disease. Blood 71: 512, 1988.

10. Zerez C R, Lachant N A, and Tanaka K R: Impaired erythrocyte methemogloblin reduction in sickle cell disease: dependence of methemoglobin reduction on reduced nicotinamide adenine dinucleotide content. Blood 76: 1008, 1990.

11. Hebbel R P, Morgan W T, Eaton J W, and Hedlund B E: Accelerated autooxidation heme loss due to instability of sickle hemoglobin. Proc Natl Acad Sci USA 85: 237, 1998.

12. Lachant N A, Zerez C R, and Tanaka K R: Relationship between the nicotinamide adenine dinucleotide redox potential and the 2,3-diphosphoglycerate content in the erythrocyte in sickle cell disease. Br J Haematol 72: 265, 1989.

13. Zerez C R, Lachant N A, Lee S j, and Tanaka K R: Decreased RBC redox potential and abnormal pyridine nucleotide content and metabolism in patients with sickle cell disease. Clin Res 35: 437A,1987.

14. Zerez C R, Savely S M, and Tanaka K R: unpublished data.

15. Zerez C R, Vadgama J V, Sayely S M, and Tanaka K R: unpublished data.

16. Enwonwu CO, Xu XX, and Turner E: Nitrogen metabolism in sickle cell anemia: Free amino acids in plasma and urine. Am J Med Sci 300: 366, 1990.

17. Zerez C R, Wong M D, Tanaka K R: Partial purification and properties of nicotinamde adenine dinucleotide synthetase from human erythrocytes: Evidence that enzyme activiy is a sensitive indicator of lead exposure. Blood 75: 1576, 1990.

18. Ziegler T R, Benfell K, Smith R J, Young L S, Brown E, Ferrari-Baliviera E, Lowe D K, Wilmore D W: Safety and metabolic effects of L-glutamine administration in humans. JPEN 14: 137s, 1990.

19. Shabert J, Ehrlich N: *The Ultimate Nutrient Glutamine: The Essential Nonessential Amino Acid,* Avery Publishing Group, Garden City Park, N.Y., pp. 97–106, 1994.

20. Niihara Y, Zerez C R, Akiyama D S, and Tanaka K R: Increased red cell glutamine availability in sickle cell anemia. I. Demonstration of a several fold increase in active glutamine transport in intact red cells. Blood 84: Suppl 1, 404a, 1994.

21. Jansen G, Koenderman L, Rijksen G, Cats BP, Staal GEJ: Characteristics of hexokinase, pyruvate kinase, glucose-6-phosphate dehydrogenase during adult and neonatal reticulocyte maturation. Am J Hematol 20: 203, 1985.

22. Zerez C R, Niihara Y, Akiyama D S, and Tanaka K R: Increased red cell glutamine availability in sickle cell anemia II. Evidence for higher affinity red cell glutamate transport and higher plasma glutamine concentration. Blood 84: Suppl 1, 411a, 1994.

23. Niihara Y, Zerez C R, Akiyama D S, and Tanaka K R: Increased red cell glutamate in sickle cell disease: Evidence that increased glutamine availability is a mechanism for increased total NAD. J Invest Med 43: Suppl 1, 131a, 1995.

24. Niihara Y, Zerez C R, Akiyama D, Tanaka K R: Elevation of redox potential in sickle red blood cells by oral administration of L-glutamine. J Invest Med 44: Suppl 1, 109a, 1996.

25. Repka T, Shalev O, Reddy R, Yuan J, Abrahamov A, Rachmilewitz E A, Low P S, Hebbel R P: Nonrandom association of free iron with membranes of sickle and β-thalassemic erythrocytes. Blood 82: 3204, 1993.

26. Hebbel R P: Membrane-associated iron, in Embury S H, Hebbel R P, Mohandas N, Steinberg M H (eds): Sickle Cell Disease: Scientifice Principles and Clinical Practice. New York, N.Y., Raven, 1994, p. 163.

27. Beutler E: *Red Cell Metabolism: A Manual of Biochemical Methods,* 3rd Edition, Grune and Stratton, Orlando, pp. 10–13, pp. 37–66, pp. 121–157; 1984.

28. Zerez C R, Lee S J, and Tanaka K R: Spectrophotometric determination of oxidized and reduced pyridine nucleotides in erythrocytes using a single extraction procedures. Anal Biochem 164: 367, 1987.

29. Erslev A J *Reticulocyte enumeration,* in William W J, Beutler E, Erslev A J, Lichtman M A (eds): Hematology 4th edition, McGraw-Hills, N.Y., pp. 1702–1703, 1990.

30. Shalev O, Repka T, Goldfarb A, Grinberg L, Abrahamov A, Olivieri N F, Rachmilewitz E A, Hebbel R P: Deferiprone (L1) chelates pathologic iron deposits from membranes of intact thalassemic and sickle red blood cells in vitro and in vivo. Blood 86: 2008, 1995.

We claim:

1. A method for treating sickle cell disease and/or thalassemia in a patient suffering therefrom, comprising the step of orally administering a safe and pharmacologically effective amount of a compound consisting essentially of L-glutamine.

2. The method of claim 1, wherein the compound is orally consumed by the patient.

3. The method of claim 1, wherein up to about 60 grams per day of L-glutamine will be orally consumed by the patient.

4. A method of treating sickle cell disease and/or thalassemia in a patient suffering therefrom, comprising the step of administering a safe and pharmacologically effective amount of a compound which comprises L-glutamine.

5. A method of treating sickle cell disease and/or thalassemia in a patient suffering therefrom, comprising the step of administering a safe and pharmacologically effective amount of a compound which comprises N-acetyl-L-glutamine.

6. A method of treating sickle cell disease and/or thalassemia in a patient suffering therefrom, comprising the step of administering a safe and pharmacologically effective amount of a compound which comprises a dipeptide containing at least one L-glutamine amino acid molecule.

7. A method for treating sickle cell disease and/or thalassemia in a patient suffering therefrom, comprising the step of orally administering a safe and pharmacologically effective amount of a compound which comprises N-acetyl-L-glutamine.

8. A method for treating sickle cell disease and/or thalassemia in a patient suffering therefrom, comprising the step of orally administering a safe and pharmacologically effective amount of a compound which comprises a dipeptide containing at least one L-glutamine amino acid molecule.

9. A method for treating sickle cell disease and/or thalassemia in a patient suffering therefrom, comprising the step of orally administering a safe and pharmacologically effective amount of a compound which comprises L-glutamine.

* * * * *

UNITED STATES PATENT AND TRADEMARK OFFICE
CERTIFICATE OF CORRECTION

PATENT NO. : 5,693,671
DATED : Dec. 2, 1997
INVENTOR(S) : Yutaka Niihara, Charles R. Zerez, Kouichi R. Tanaka It is certified that error appears in the above-identified patent and that said Letters Patent is hereby corrected as shown below:

Title page: Inventor: change "Yukaka", to read --Yutaka--.

Signed and Sealed this

Tenth Day of March, 1998

Attest:

BRUCE LEHMAN

Attesting Officer

Commissioner of Patents and Trademarks